Feb. 25, 1969 M. A. MILLER Plant Pat. 2,868
GERANIUM PLANT
Filed March 9, 1967
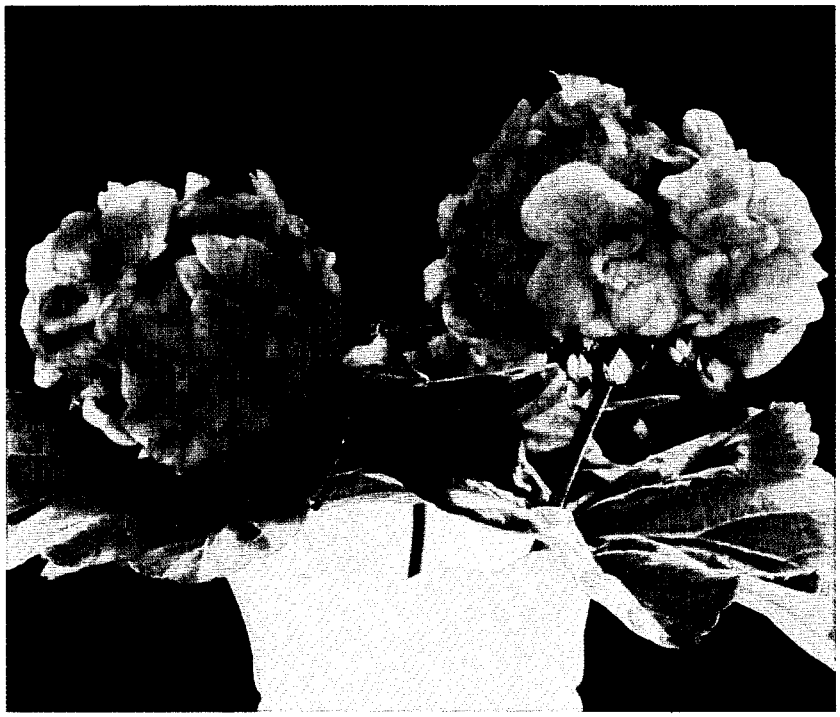
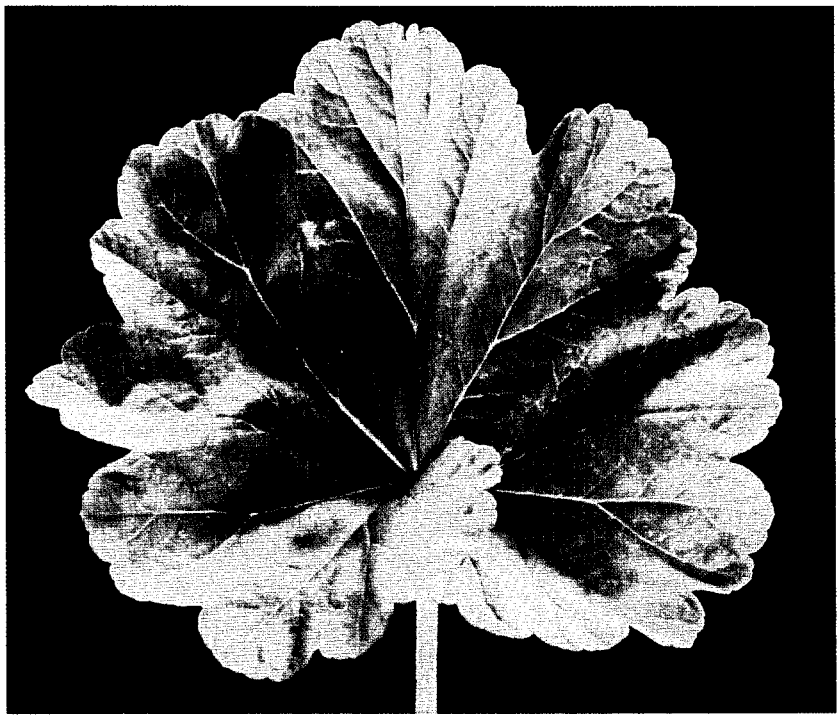
INVENTOR
MARK A. MILLER
BY McCoy, Greene & Howell
ATTORNEYS United States Patent Office Plant Pat. 2,868
Patented Feb. 25, 1969

2,868

GERANIUM PLANT

Mark A. Miller, State Route 113 E.,
Milan, Ohio 44846

Filed Mar. 9, 1967, Ser. No. 622,027
U.S. Cl. Plt.—68 1 Claim
Int. Cl. A01h 5/02

ABSTRACT OF THE DISCLOSURE

A geranium plant characterized particularly by its healthy growth, long lasting globular truss, velvety purple florets, and large, super-orbiculate leaves with overlapping bases.

The present discovery relates to a new and distinct variety of geranium plant. The new and patentable characteristics thereof reside in its healthy growth, its unusual brilliant purple and long-lasting globular truss, and its leaves which are unusually large and super-orbiculate, overlapping at their bases.

It was discovered by me during experiments carried on by me in Milan High School at Main Street, Milan, Ohio. My experiments were to produce mutants of geranium plants. The present plant was the result of cross-breeding two varieties, the identification of which I am not certain. It has been asexually reproduced several times and its qualities have proven permanent.

The drawings show the leaf and flower of a fully developed geranium plant of the new variety claimed.

*The plant*

Growth: Very bushy, vigorous, and compact. Attains an average size of 12 to 18 inches as a pot plant. Produces a large number of florets which are long lasting and form a more globular truss than most other types.

Blooming habit: Free and continuous bloomer, both because of its large number of "breaks" and its tendency to recover quickly after cuttings are taken.

Inflorescence: Large, relatively globular, umbel or truss on long, upright peduncle extending clearly above foliage, and measuring 4–5 inches in diameter.

Foliage:

*Quantity.*—Abundant.
*Size.*—Very large, 5–7 inches across.

*Color.*—Medium green.
*Shape.*—Super-orbiculate, overlapping at base, disc to cup shaped, undulate and deeply lobed.
*Texture.*—Firm, medium thickness, heavy velvety surface.
*Stem.*—Long, strong.
*Peduncle.*—Longer and stronger than stem, upright and relatively straight.

*The flower*

Truss:

*Size.*—Large, 4–5 inches in diameter.
*Shape.*—Compact and more globular than most varieties.
*Number of florets.*—Variable, 25–30 is average.
*Lasting quality.*—Exceptionally long lasting. Blooms remain open up to 2 weeks under normal conditions, longer if kept dry.

Bud:

*Sepals.*—Long and pointed.
*Color.*—Tyrian purple 727 and 727/2 (The Royal Horticultural Society Horticultural Color Chart).
*Form.*—Pointed.

Florets:

*Size.*—Approximately 1–1¼ inches diameter.
*Petalage.*—Double.
*Color.*—Tyrian purple 727 to 727/2 with a fleck of Geranium Lake 20 to 20/1 at the base of each petal (Royal Horticultural Society Horticultural Color Chart). Colors are very brilliant.
*Texture.*—Velvety.
*Form.*—Resembling a rose.
*Lasting quality.*—Excellent. Average floret lasts up to 2 weeks.
*Behavior.*—Soft and luxuriant appearing.

Having thus disclosed my invention, I claim:

1. A new and distinct variety of geranium plant, substantially as shown and described, characterized particularly by its healthy growth; its long lasting globular truss, its distinctive velvety purple florets; and its large super-orbiculate leaves with overlapping bases.

No references cited.

ROBERT E. BAGWILL, *Primary Examiner.*

UNITED STATES PATENT OFFICE

CERTIFICATE OF CORRECTION

February 25, 196

Plant Patent No. 2,868

Mark A. Miller

It is certified that error appears in the above identified patent and that said Letters Patent are hereby corrected as shown below:

Column 2, line 20, "and" should read -- to --.

Signed and sealed this 24th day of March 1970.

(SEAL)
Attest:

Edward M. Fletcher, Jr.
Attesting Officer

WILLIAM E. SCHUYLER, JR.
Commissioner of Patents